(12) United States Patent
Cewers

(10) Patent No.: US 10,682,489 B2
(45) Date of Patent: Jun. 16, 2020

(54) TURBINE VENTILATOR SYSTEM AND METHOD

(71) Applicant: Transunit AB, Malmö (SE)

(72) Inventor: Göran Cewers, Limhamn (SE)

(73) Assignee: TRANSUNIT AB, Malmö (SE)

( * ) Notice: Subject to any disclaimer, the term of this patent is extended or adjusted under 35 U.S.C. 154(b) by 1063 days.

(21) Appl. No.: 15/037,872

(22) PCT Filed: Nov. 20, 2014

(86) PCT No.: PCT/EP2014/075214
§ 371 (c)(1),
(2) Date: May 19, 2016

(87) PCT Pub. No.: WO2015/075156
PCT Pub. Date: May 28, 2015

(65) Prior Publication Data
US 2016/0287833 A1    Oct. 6, 2016

(30) Foreign Application Priority Data

Nov. 20, 2013 (SE) ...................................... 1351378

(51) Int. Cl.
*A61M 16/20* (2006.01)
*A61M 16/00* (2006.01)
*A61M 16/10* (2006.01)

(52) U.S. Cl.
CPC ...... *A61M 16/204* (2014.02); *A61M 16/0066* (2013.01); *A61M 16/0075* (2013.01);
(Continued)

(58) Field of Classification Search
CPC .............. A61M 16/00; A61M 16/0003; A61M 16/0057; A61M 16/0066; A61M 16/0075; A61M 16/0078; A61M 16/1075; A61M 16/20; A61M 16/201; A61M 16/204; A61M 16/208; A61M 2016/0015; A61M 2016/0018; A61M 2016/0021; A61M 2016/0027; A61M 2016/0039;
(Continued)

(56) References Cited

U.S. PATENT DOCUMENTS 3,664,361 A * 5/1972 Bartels .................. A61M 16/12
137/98
4,060,077 A * 11/1977 Friedman .......... A61M 16/0051
128/205.16

(Continued)

*Primary Examiner* — Justine R Yu
*Assistant Examiner* — Matthew R Moon
(74) *Attorney, Agent, or Firm* — Kagan Binder, PLLC

(57) ABSTRACT

The present invention relates to a turbine ventilator having a fast response to the required inhalation of a subject connected to the ventilator. The turbine ventilator (1000) comprises: a first valve (3) connectable to at least one breathing orifice of the subject; an inspiratory reservoir (6) having an adjustable volume, said inspiratory reservoir being fluidically connectable to said first valve; a turbine unit (1) fluidically connectable to the inspiratory reservoir, said turbine unit being fluidically connectable via said first valve to the at least one breathing orifice of the subject; and a control unit (9) configured to control said first valve for controlling a flow or pressure from the inspiratory reservoir and/or turbine unit to the subject based on setpoints.

13 Claims, 7 Drawing Sheets

(52) U.S. Cl.
CPC ...... *A61M 16/1075* (2013.01); *A61M 16/208* (2013.01); *A61M 16/0078* (2013.01); *A61M 2016/0018* (2013.01); *A61M 2016/0021* (2013.01); *A61M 2016/0027* (2013.01); *A61M 2016/0039* (2013.01); *A61M 2016/0042* (2013.01); *A61M 2205/3331* (2013.01); *A61M 2205/3334* (2013.01); *A61M 2205/3355* (2013.01); *A61M 2205/3379* (2013.01); *A61M 2205/3606* (2013.01); *A61M 2205/3666* (2013.01); *A61M 2205/42* (2013.01); *A61M 2205/50* (2013.01)

(58) Field of Classification Search
CPC .. A61M 2016/0042; A61M 2205/3331; A61M 2205/3334; A61M 2205/3355; A61M 2205/3379; A61M 2205/3606; A61M 2205/3666; A61M 2205/42; A61M 2205/50
See application file for complete search history.

(56) References Cited

U.S. PATENT DOCUMENTS

| | | | | |
|---|---|---|---|---|
| 4,224,940 A | * | 9/1980 | Monnier | A61M 16/021 128/205.16 |
| 4,430,995 A | * | 2/1984 | Hilton | A61M 16/0057 128/204.21 |
| 5,299,579 A | * | 4/1994 | Gedeon | A61B 5/083 128/205.14 |
| 5,492,115 A | * | 2/1996 | Abramov | A61H 31/00 128/205.24 |
| 5,497,767 A | * | 3/1996 | Olsson | A61M 16/00 128/205.13 |
| 6,095,139 A | | 8/2000 | Psaros | |
| 6,131,571 A | | 10/2000 | Lampotang et al. | |
| 6,739,335 B1 | | 5/2004 | Rapport et al. | |
| 8,161,970 B2 | * | 4/2012 | Cewers | A61M 16/12 128/204.21 |
| 2005/0217672 A1 | | 10/2005 | Bengtsson et al. | |
| 2007/0062531 A1 | * | 3/2007 | Fisher | A61B 5/083 128/204.23 |
| 2007/0163588 A1 | | 7/2007 | Hebrank et al. | |
| 2007/0163592 A1 | | 7/2007 | Reinstadtler et al. | |
| 2009/0173348 A1 | * | 7/2009 | Fisher | A61B 5/083 128/205.12 |
| 2010/0163046 A1 | | 7/2010 | Fisher et al. | |
| 2010/0170513 A1 | | 7/2010 | Bowditch et al. | |
| 2011/0284002 A1 | * | 11/2011 | Cewers | A61M 16/0057 128/204.21 |
| 2016/0228670 A1 | * | 8/2016 | Av-Gay | G16H 40/63 |

* cited by examiner

TURBINE VENTILATOR SYSTEM AND METHOD

CROSS-REFERENCE TO RELATED APPLICATIONS

This application claims priority to International Application No. PCT/EP2014/075214, filed Nov. 20, 2014, and titled "A TURBINE VENTILATOR SYSTEM AND METHOD", which in turn claims priority from European Application having serial number 1351378-3, filed on Nov. 20, 2013, both of which are incorporated herein by reference in their entireties.

BACKGROUND OF THE INVENTION

Field of the Invention

This disclosure pertains in general to the field of ventilators. More particularly the disclosure relates to medical ventilation which includes a bellow and a turbine unit.

Description of the Prior Art

Medical ventilator based on a turbine, such as a blower or fan, has the advantages that they do not require any high pressure gas. Thus they can be used as alternatives to low pressure ventilators when there is no access to high pressure gas, such as form a compressor or a tub. Medical ventilator using a turbine has some drawbacks. One of those drawbacks is that there will be transients in the flow before the turbine reaches full speed and can provide the needed flow of inspiratory gas to the subject connected to the ventilator.

U.S. Pat. No. 6,131,571 discloses a combination ventilation apparatus and anaesthesia delivery system. A mixture of air, oxygen, nitrous oxide or other clinical gas and anaesthetics, are circulated by a variable speed centrifugal blower. Constant circuit volume is maintained by computer control of gas make-up valves in response to the movement of a weighted bellows located between the proportional flow control valve and centrifugal blower. There is no disclosure of how to avoid transients in the flow before the turbine reaches full speed and can provide the needed flow of inspiratory gas to the subject connected to the ventilator.

U.S. Pat. No. 6,739,335 discloses method and apparatus for optimizing the controlled positive pressure in treating sleep disordered breathing. In one example of the disclosed systems, a reservoir bag is used to reduce transience in the flow and pressure. It is not disclosed when or why transience appears nor how the reservoir bag is used to reduce them. The document does not disclose how to obtain a full flow fast, before the turbine reaches full speed and can provide the needed flow of inspiratory gas to the subject connected to the ventilator.

US 2007/0163592 discloses gas reservoir bag comprising a flexible bag for separating two different gases with a connection. The system has two turbines, to generate both a positive and a negative airway pressure. It is not disclosed how to connect the reservoir bag and the turbines to avoid achieves ant achieve a fast response Hence, a new improved design of a medical ventilator would be advantageous. Especially a medical ventilator having a fast response to the required inhalation of a subject connected to the ventilator.

SUMMARY OF THE DISCLOSURE

Accordingly, examples of the present disclosure preferably seek to mitigate, alleviate or eliminate one or more deficiencies, disadvantages or issues in the art, such as the above-identified, singly or in any combination by providing a device or method according to the appended patent claims for providing a fast response ventilator using a turbine unit and an inspiratory reservoir, such as a bellow.

According to one aspect of the disclosure, a turbine ventilator is described. The turbine ventilator comprises a first valve connectable to at least one breathing orifice of a subject. The turbine ventilator further comprises an inspiratory reservoir having an adjustable volume, the inspiratory reservoir is fluidically connectable to the first valve at least one breathing orifice of a subject. A turbine unit is fluidically connectable to the inspiratory reservoir, and the turbine unit is fluidically connectable via the first valve to the at least one breathing orifice of the subject. A control unit is configured to control the first valve for controlling a flow or pressure from the inspiratory reservoir and/or turbine unit to the subject based on setpoints.

In an example of the disclosure, the turbine ventilator further comprising a second valve arranged between the turbine unit and the inspiratory reservoir. The control unit is configured to control the second valve to control a flow or pressure from the turbine unit to the inspiratory reservoir.

By being able to provide flow from both a turbine unit and an inspiratory reservoir, a fast response may be obtained.

In some examples of ventilator, the control unit is configured to adjust the first valve and/or the second valve, thereby fluidically connecting the turbine unit and the inspiratory reservoir to the at least one breathing orifice of the subject. Additionally, the control unit is configured to fluidically connecting the turbine unit to the at least one breathing orifice of the subject. Additionally, the control unit is configured to fluidically connecting the turbine unit to the inspiratory reservoir and to the at least one breathing orifice of the subject. Additionally, the control unit is configured to fluidically connecting the turbine unit to the inspiratory reservoir.

In some examples, the ventilator comprises a support element which is arranged on one side of the inspiratory reservoir. The turbine unit is then mounted on the support element whereby vibrations and/or heat from the turbine unit are isolated from the environment by the inspiratory reservoir.

According to a further aspect of the disclosure, a method for fast response turbine ventilator is disclosed. The method comprising providing an inspiratory reservoir having an adjustable volume, the inspiratory reservoir is fluidically connectable to a first valve being connected to at least one breathing orifice of a subject. The method further includes, providing a turbine unit which is fluidically connectable to the inspiratory reservoir. The turbine unit is also fluidically connectable to the first valve being connected to at least one breathing orifice of the subject. The method then includes controlling the first valve for controlling a flow or pressure from the inspiratory reservoir and/or turbine unit to the subject based on setpoints.

According to another aspect of the disclosure, a method for fast response turbine ventilator id disclosed. The method comprises measuring a flow or pressure of a fluid to a subject by at least one sensor. The method further includes controlling a first valve for controlling a flow or pressure from an inspiratory reservoir and a turbine unit to the subject based on setpoints for the flow or pressure measure by the sensors.

"comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which examples of the disclosure are capable of will be apparent and elucidated from the following description of examples of the present disclosure, reference being made to the accompanying drawings, in which.

DESCRIPTION OF PREFERRED EXAMPLES

Figure 1:
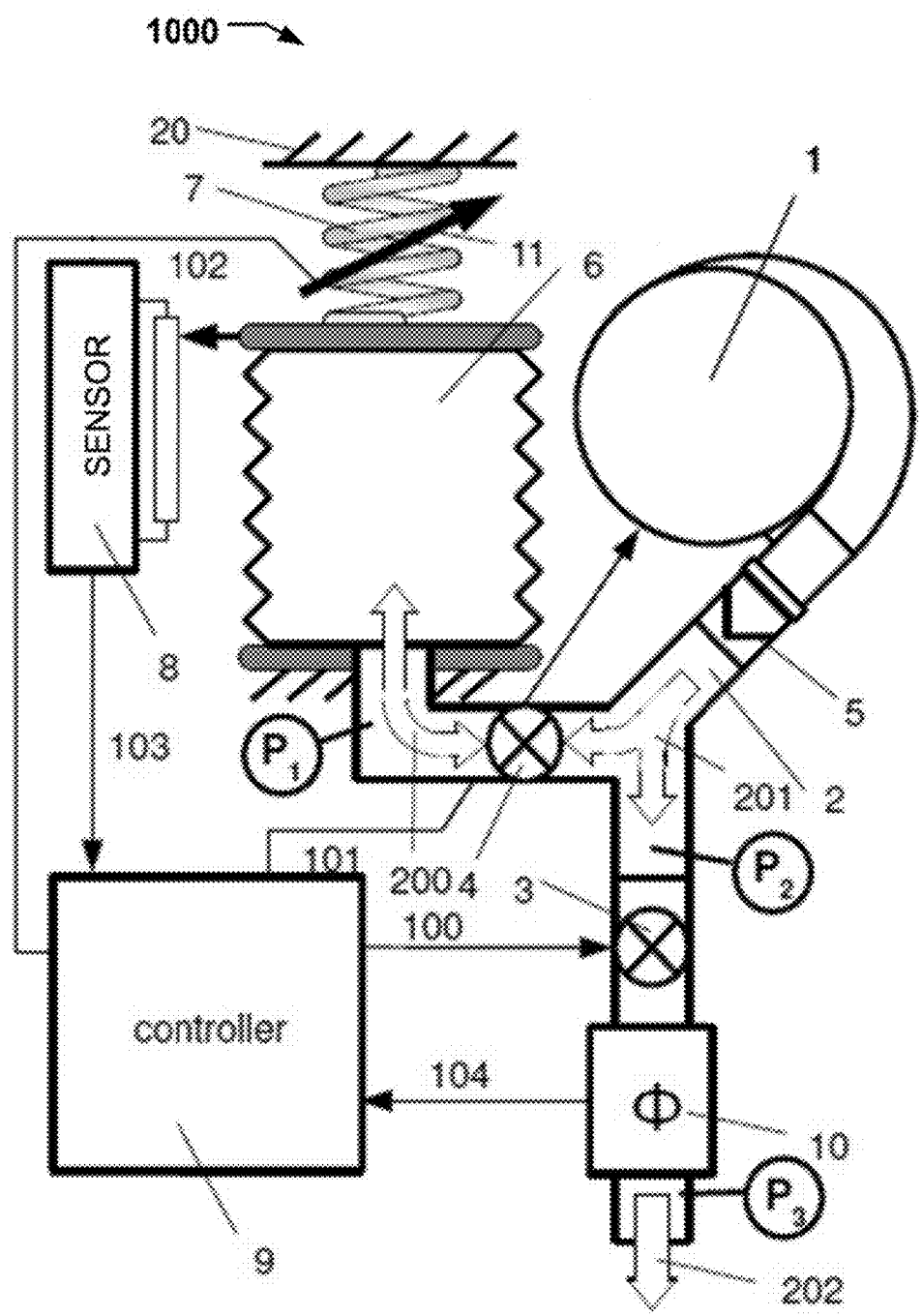
FIG. 1 is illustrating an exemplary configuration of a turbine ventilator.

Specific examples of the disclosure will be described with reference to the accompanying drawings. This disclosure may, however, be embodied in many different forms and should not be construed as limited to the examples set forth herein; rather, these examples are provided so that this disclosure will be thorough and complete, and will fully convey the scope of the disclosure to those skilled in the art. The terminology used in the detailed description of the examples illustrated in the accompanying drawings is not intended to be limiting of the disclosure. In the drawings, like numbers refer to like elements.

The following description focuses on examples of the present disclosure applicable to a medical ventilator or respirator, specifically a turbine driven ventilator, such as a blower ventilator. However, it will be appreciated that the disclosure is not limited to this application but may be applied to many other systems where a medical ventilator is required.

FIG. 1 is illustrating an exemplary configuration of a turbine ventilator 1000. The ventilator comprises a turbine unit 1, such as a blower or a fan, an inspiratory reservoir 6, such as a bag or a bellow. The turbine unit 1 and the inspiratory reservoir 6 are connectable to a subject by a three way channel 2. The ventilator further comprises a control unit 9 for controlling the inspiratory flow or pressure from the turbine unit 1 and/or the inspiratory reservoir 6 to a subject connected to the ventilator based on setpoints. Additionally, in some examples, the control unit 9 may be configured to coupling the at least a part of the flow from the turbine unit 1 to the inspiratory reservoir 6.

The controlling of the flow or pressure from the turbine unit 1 to the subject, or to the inspiratory reservoir 6, and the controlling of the flow or pressure from the inspiratory reservoir 6 to the subject may be performed by valves.

In the example illustrated in FIG. 1, three valves are used an inhalation valve 3, an inspiratory reservoir valve 4 and a check valve 5.

In other examples at least two valves are used, a first valve (i.e. an inspiratory reservoir valve 4) arranged between the turbine unit and the inspiratory reservoir and a second valve (i.e. inhalation valve 3) arranged between the turbine unit and the subject.

In some other examples only one valve is sued, such as an inhalation valve 3, to control the flow and or pressure.

Figure 2:
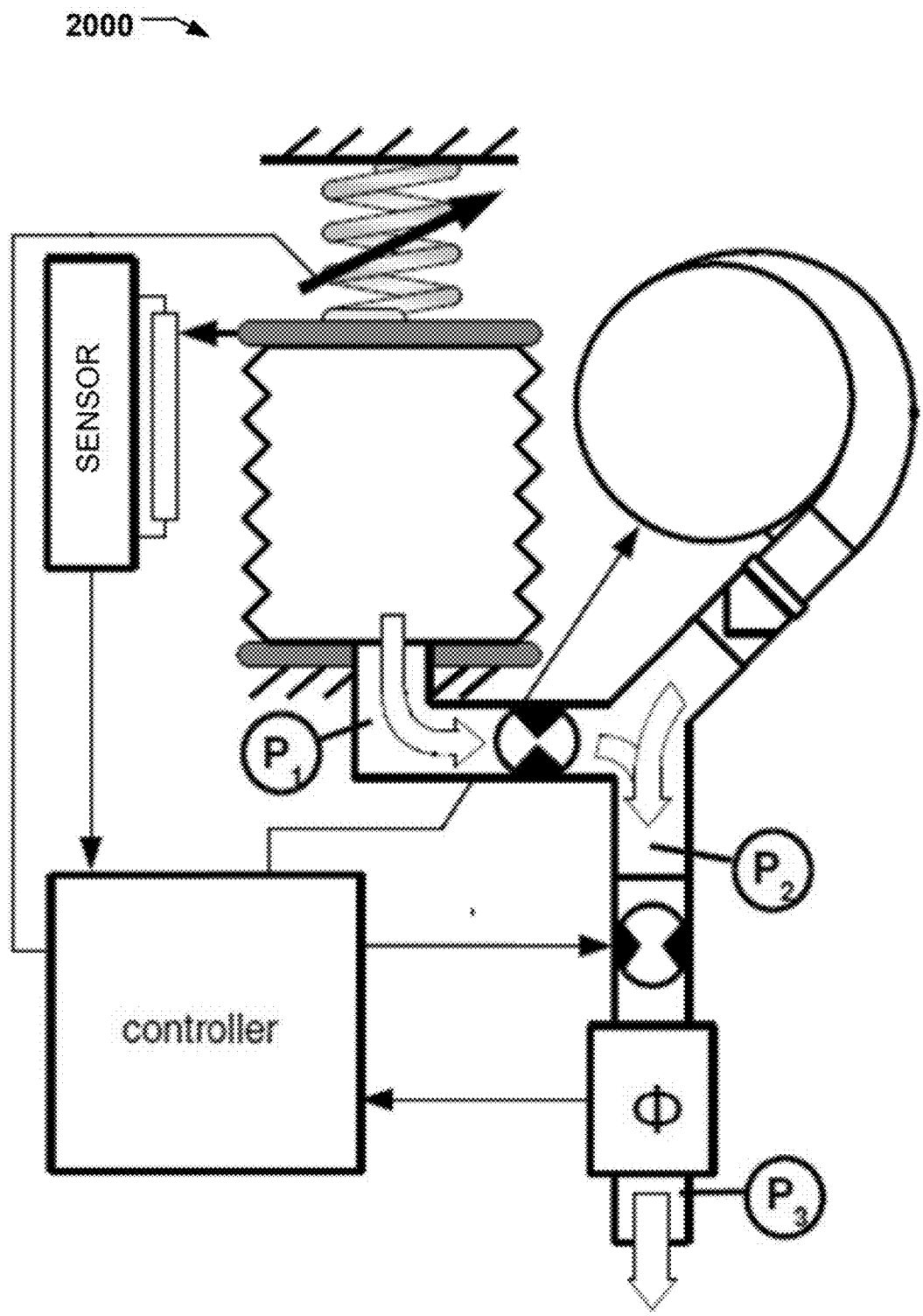
FIG. 2 is illustrating an exemplary configuration wherein a turbine unit is connected to an inspiratory reservoir and both are connected a subject, during an inspiratory phase.

By controlling the valves, the turbine unit 1 may be fluidically connected to the inspiratory reservoir 6. Further, by controlling the valves the turbine unit 1 may be fluidically connected to the subject. Hence different modes can be set. Some examples are:

Fluidically connect a turbine flow 201 from the turbine unit 1 and an inspiratory reservoir flow 200 from the inspiratory reservoir 6 to the subject by opening an inspiratory reservoir valve 4 and the inhalation valve 3, as illustrated by the arrows for the ventilator 2000 in FIG. 2. This will combine the inspiratory reservoir flow 200 and the turbine flow 201 into an inhalation flow 202.

Figure 3:
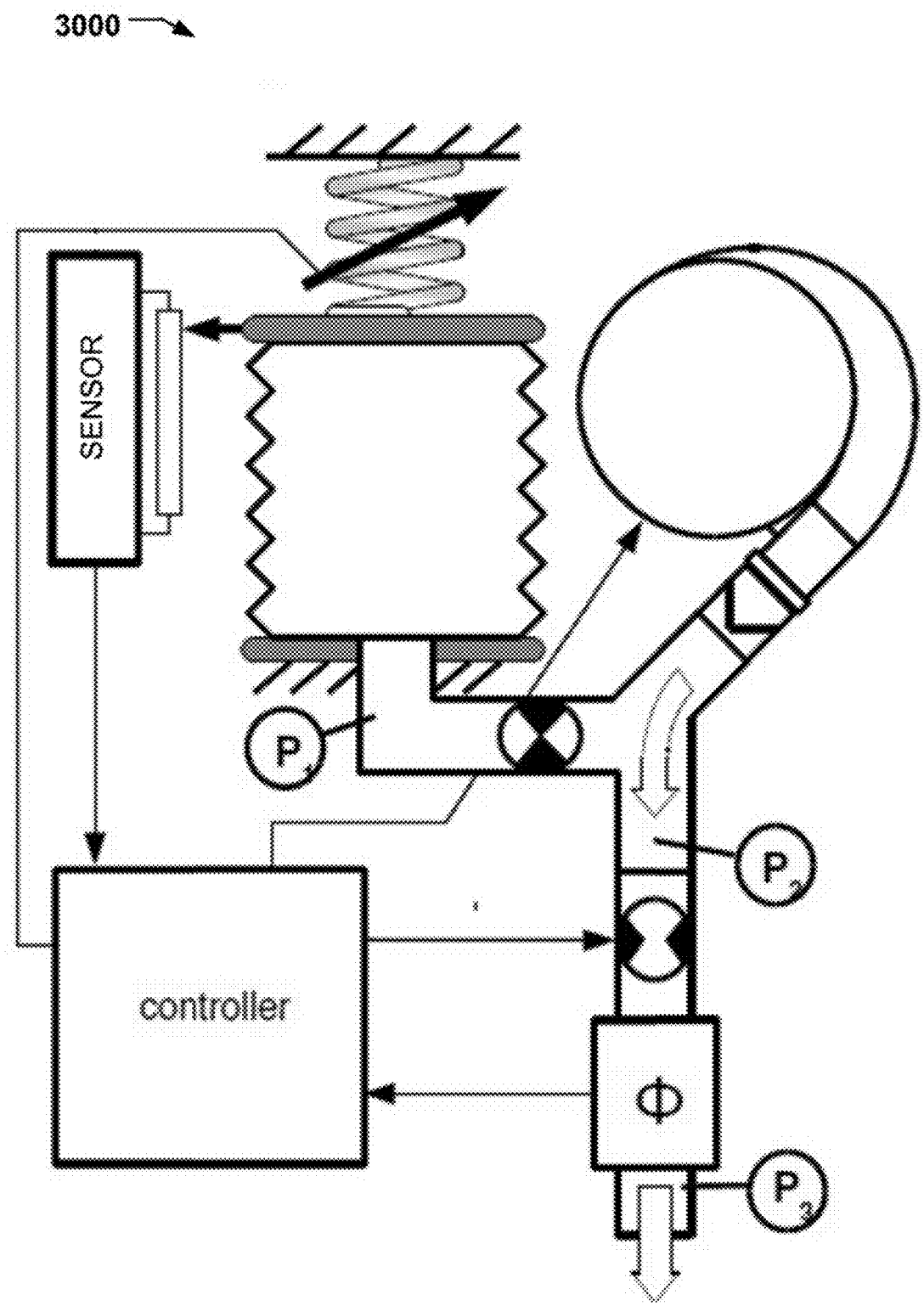
FIG. 3 is illustrating an exemplary configuration wherein a turbine unit is connected to a subject, during an inspiratory phase.

Fluidically connect only a turbine flow 201 from the turbine unit 1 to the subject by closing an inspiratory reservoir valve 4 and opening inhalation valve 3, as illustrated by the arrows for the ventilator 3000 in FIG. 3. Here the inhalation flow 202 is the same as the turbine flow 201.

Figure 4:
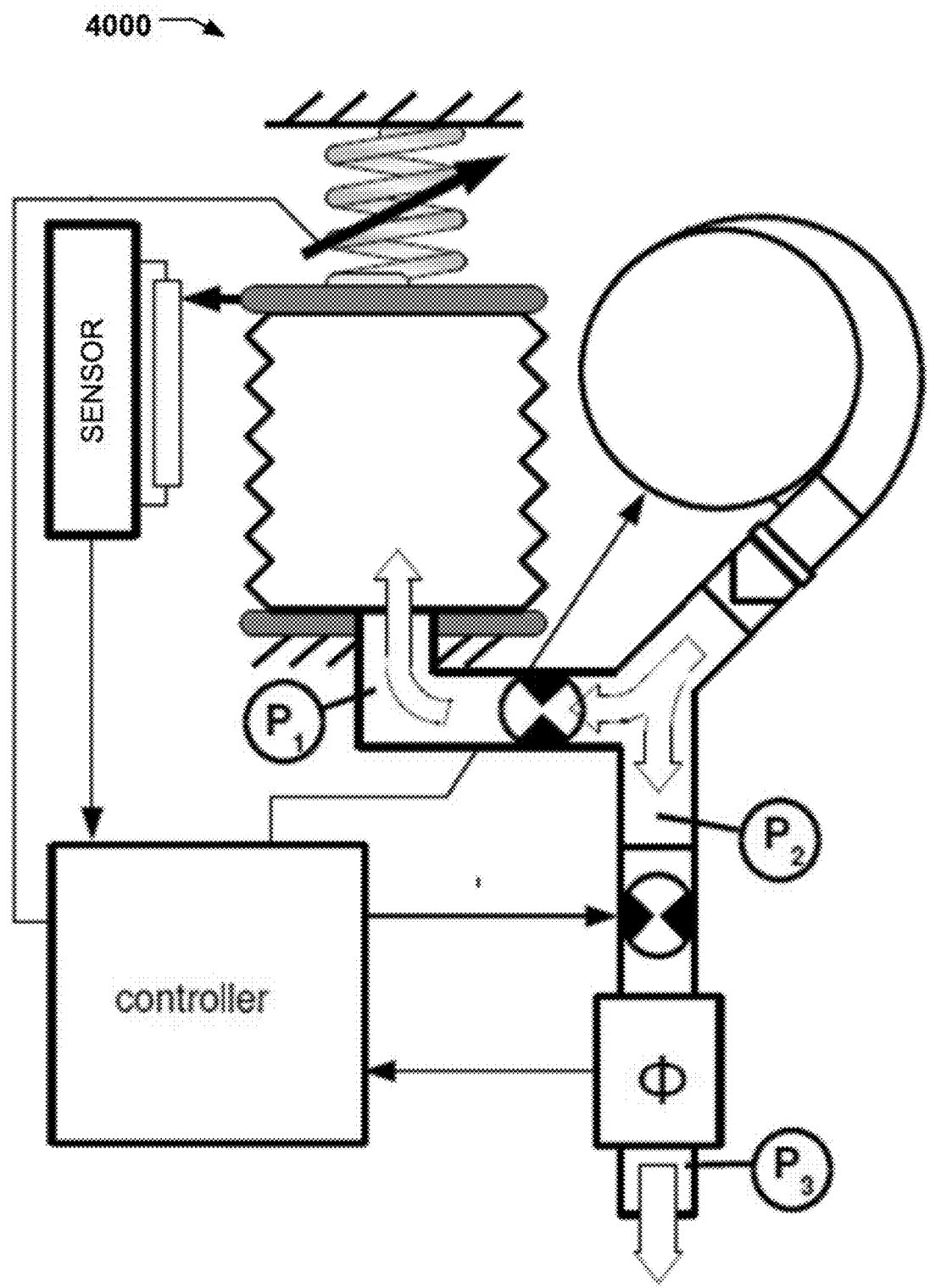
FIG. 4 is illustrating an exemplary configuration wherein a turbine unit is connected to an inspiratory reservoir and to a subject, during an inspiratory phase.

Fluidically connect a turbine flow 201 from the turbine unit 1 to the inspiratory reservoir 6 and to the subject by opening an inspiratory reservoir valve 4 so that part of the turbine flow 201 from the turbine unit 1 may flow through and opening inhalation valve 3 and part of the turbine flow 201 is the inhalation flow 202, as illustrated by the arrows for the ventilator 4000 in FIG. 4.

Figure 5:
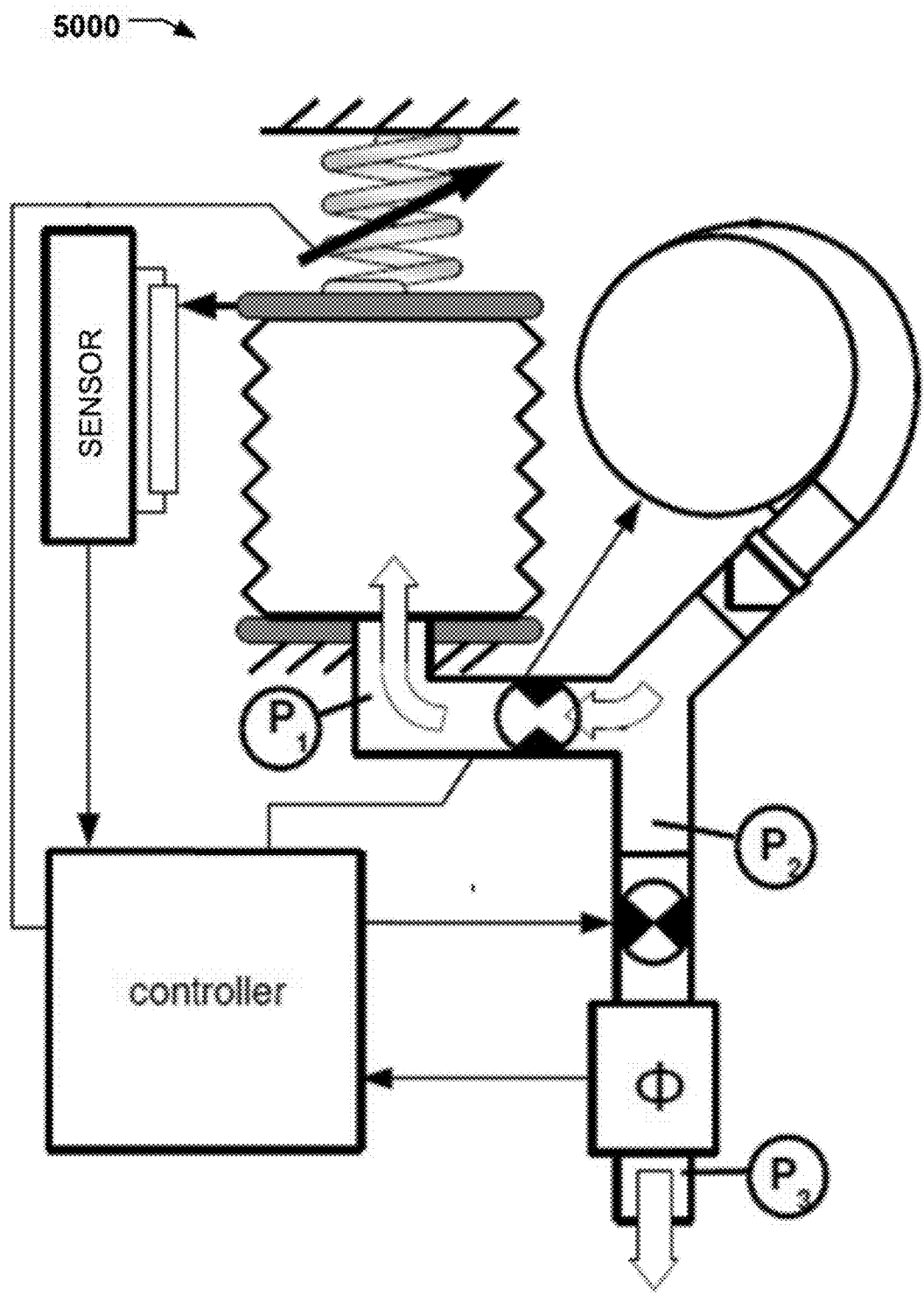
FIG. 5 is illustrating an exemplary configuration wherein a turbine unit is only connected to an inspiratory reservoir.

Fluidically connect a turbine flow 201 from the turbine unit 1 to only the inspiratory reservoir 6 by opening an inspiratory reservoir valve 4 so that the turbine flow 201 from the turbine unit 1 may flow through the an inspiratory reservoir valve 4 and closing inhalation valve 3, as illustrated by the arrows for the ventilator 5000 in FIG. 5.

Additionally and/or alternatively, in some examples of the disclosure, the inspiratory reservoir 6 may be a bellow which is spring-loaded by a spring 7. The spring 7 may be connected to a spring fundament 20. In the examples illustrated, the top plate of the inspiratory reservoir 6 is spring-loaded but other sides area equally viable, such as the bottom plate. The force of the spring may be adjustable using spring adjustment means 11. The spring adjustment means 11 may be adjusted either manually or by a motor. The value of the spring load may be transmitted to the control unit 9 by a spring control signal 102. The spring control signal 102 may be used to adjust the force of the spring-load if the adjustment is done by a motor.

The force of the spring 7 is preferably constant independent of the fill ratio of the volume of the bellow. By adjusting the force of the spring-load using the spring adjustment means 11, the maximum inspiratory pressure may be set.

Additionally and/or alternatively, in some examples of the ventilator, a filling ratio of the volume of the inspiratory reservoir 6 may be measured using a sensor 8, such as a potentiometer. The measured value may be transmitted to the control unit 9 by a volume signal 103. This measured value may be used to determine the fill ratio of the inspiratory reservoir 6 when the flows of the ventilator are regulated by the control unit 9.

In some examples, the volume signal 103 may be used in a feedback loop to control and provide the desired flow to the connected patient.

As the turbine unit in the disclosed system only works depending on demand, the system may generate less heat than a conventional system. In many conventional systems, the turbine unit continuously works on a high speed and any surplus of gas is re-circulated to meet a demand.

The inspiratory reservoir valve 4 is controlled by transmitting an inspiratory reservoir control signal 101 from the control unit 9 and the inhalation valve 3 are controlled by transmitting an inhalation valve control signal 100 from the control unit 9.

Additionally and/or alternatively, in some examples, the ventilator may also include an inhalation flow sensor 10 which transmits as inhalation flow signal 104 to the control unit 9 to be used for controlling the flow of the ventilator.

In some examples, the flow signal 104 may be used in a feedback loop to control and provide the desired flow to the connected patient.

Additionally and/or alternatively, in some examples, the ventilator further includes an inspiratory reservoir pressure sensor P1, a turbine pressure sensor P2, and a subject pressure sensor P3. The pressure sensor P1 is arranged to measure the pressure from the inspiratory reservoir 6. The pressure sensor P2 is arranged to measure the pressure from the turbine unit 1. Further, the pressure sensor P3 is arranged to measure a pressure of the subject connected to the ventilator.

In some examples, the pressure signals may be used in a feedback loop to control and provide the desired flow or pressure to the connected patient.

At the beginning of an inspiratory phase, the inspiratory reservoir 6 is filled with an inspiratory gas.

When the ventilator detects a new inspiration, by the subject connected to the ventilator, the turbine unit 1 will start. If the setpoints are larger than the turbine flow 201 produced by the turbine unit 1, the inspiratory reservoir valve 4 will be opened whereby an inspiratory reservoir flow 200 from the inspiratory reservoir 6 will be added and combined with the turbine flow 200 to generate an inhalation flow 202, see FIG. 2. A fast response from the ventilator is therefore possible to compensate for the reduced flow from the turbine unit 1 from start up until it may a high enough flow.

When the turbine unit 1 produces a turbine flow 200 which is the same as the setpoints the inspiratory reservoir valve 4 will be closed and only the turbine flow 200 from the turbine unit 1 will be connected to the subject, see FIG. 3.

When the turbine unit 1 produces a turbine flow 200 which is higher than the setpoints the turbine flow 200 will be used both for filling the inspiratory reservoir 6 and as inhalation flow 202 to the subject connected to the ventilator, see FIG. 4. In some examples, the inspiratory reservoir 6 may be filled by the turbine flow 200 during the expiration phase of the subject connected to the ventilator.

The inhalation valve 3 is closed during the expiratory phase. Alternatively, if a bypass flow is wanted the inhalation valve 3 may be open also during the expiratory phase.

The inspiratory reservoir valve 4 may be closed when the inspiratory reservoir 6 is full and no further flow is needed. Alternatively, in some examples of ventilator, the inspiratory reservoir valve 4 may be omitted. If the inspiratory reservoir valve 4 is omitted, the turbine unit 1 has to work against a higher pressure which will decrease the efficiency of the turbine unit 1.

Further, in some examples of the ventilator, the pressure sensor P2 may be omitted and replaced, for example, by a flow channel with a check valve from the turbine unit 1 to the inspiratory reservoir 6.

The control unit 9 regulates the turbine valve 3, the inspiratory reservoir valve 4, and the flow from the turbine unit 1 based on setpoints for the pressure and/or the flow measured by the pressure sensors, P1, P2, P3 or the flow sensors, such as the inhalation flow sensor 10. Additionally, the spring-load of the spring may be set based on setpoints for the pressure and/or the flow measured by the pressure sensors, P1, P2, P3 or the flow sensors, such as the inhalation flow sensor 10.

Additionally and/or alternatively, some examples of the system, further sensors may be used, such as further pressure sensors, flow sensors or a tachometer for the turbine unit 1.

Figure 7A:
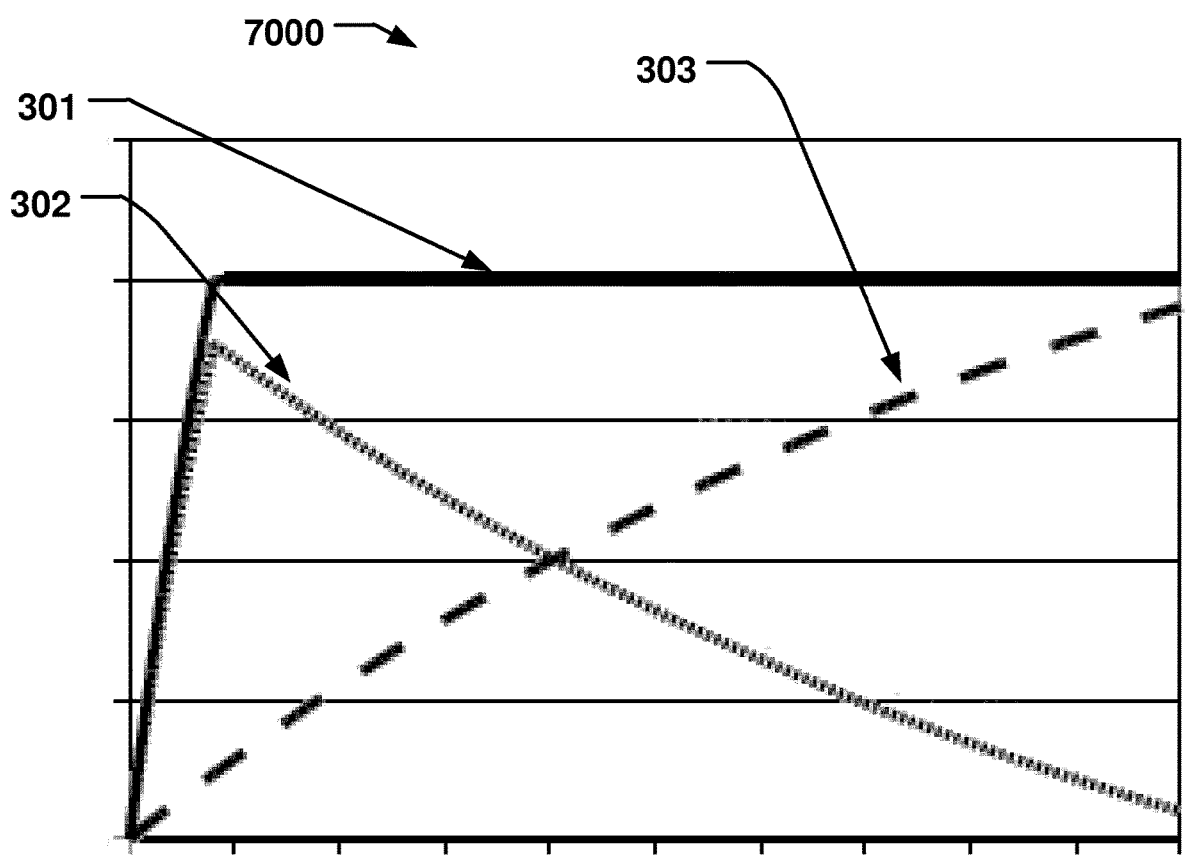
FIG. 7A is illustrating an exemplary total flow to a subject as the sum of the flows from a turbine unit and a inspiratory reservoir.

In FIG. 7A is a diagram 7000 illustrated showing volume per time as a function of time. The curve 301 illustrates the total flow to the subject. The total flow 301 wanted is equal to the combined flow form the turbine unit illustrated in curve 303 and the flow form the inspiratory reservoir illustrated in curve 302. As illustrated in this diagram, it will take some time until the flow from the turbine unit in curve 303 reached the total flow 301 wanted. This is compensated for by the flow from the 302 from the inspiratory reservoir, hence a fast response is possible. If the inspiratory reservoir is spring-loaded, the response can be adjusted by the adjusting the force of the load.

Figure 7B:
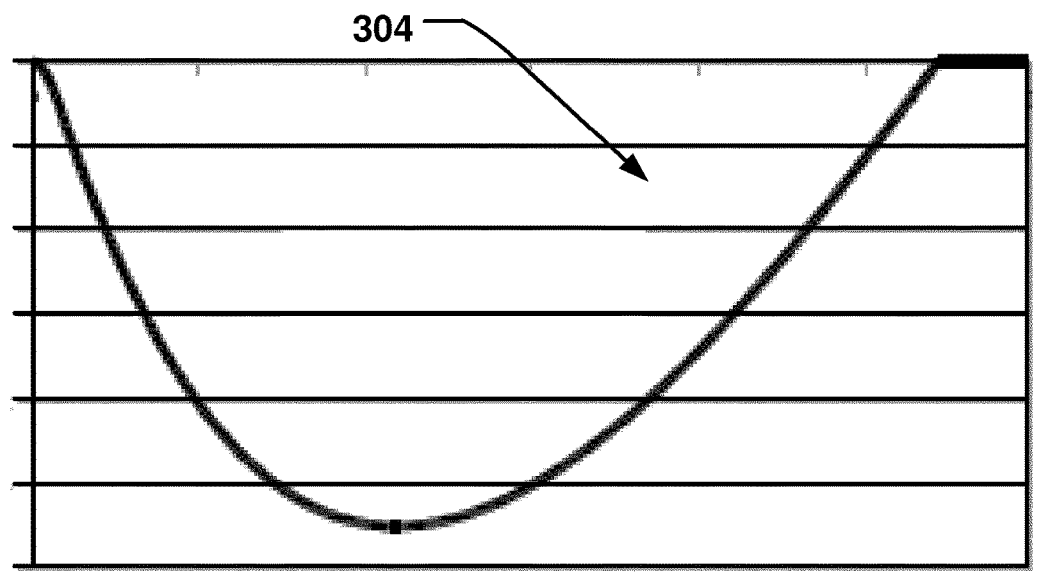
FIG. 7B is illustrating an exemplary change of volume in an inspiratory reservoir during a fast inspiratory phase.

In FIG. 7B is a diagram 8000 over the volume loss of the inspiratory reservoir illustrated, showing volume as a function of time. At the start and the end of the curve 304, which covers an inspiratory phase, the inspiratory reservoir is full. When the flow form the turbine unit needs to be compensated for to reach the total flow wanted, the volume will be reduced. As soon as the turbine unit produces a higher flow than the total flow wanted, the volume of the inspiratory reservoir will start to fill up.

Figure 6:
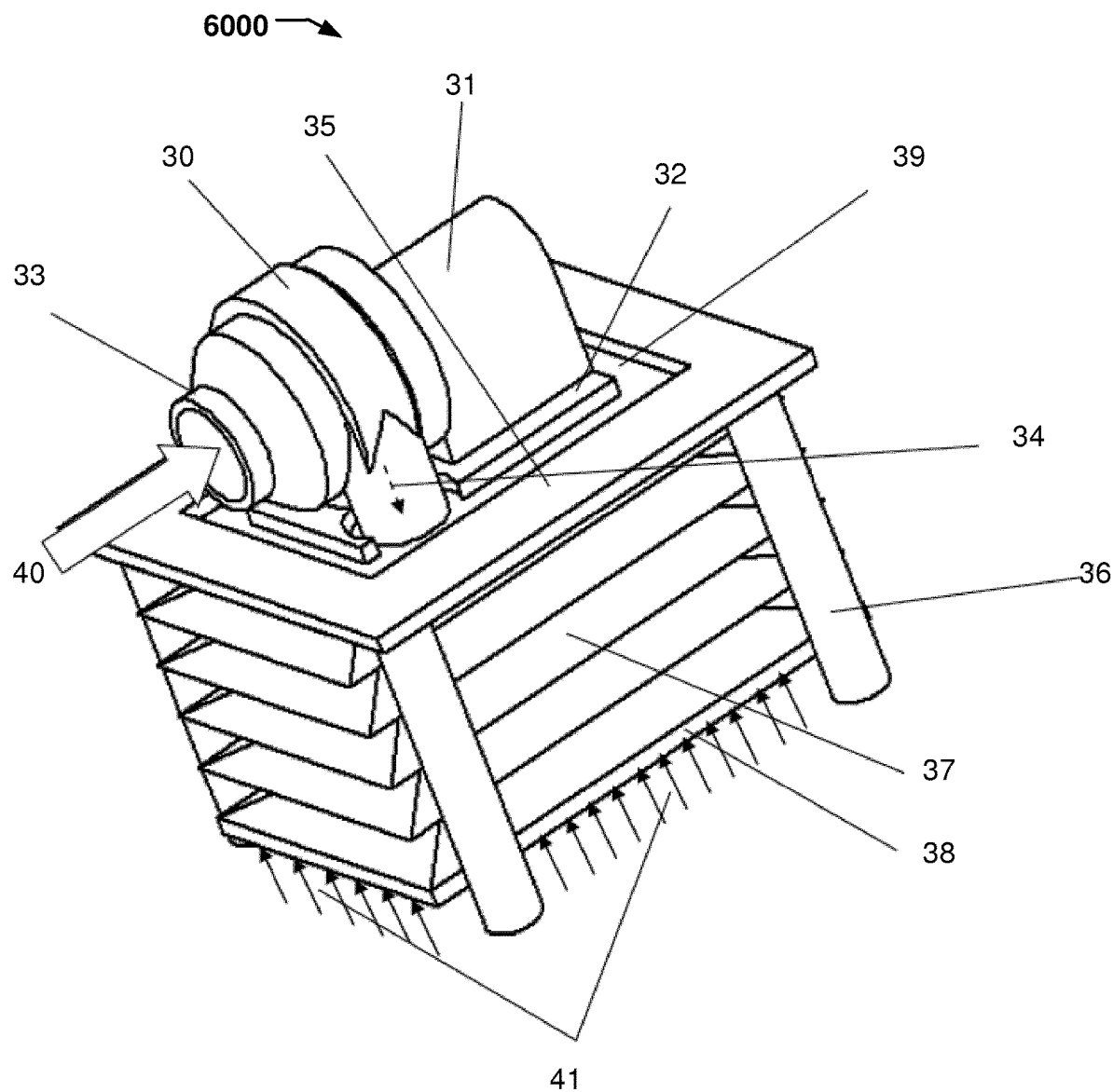
FIG. 6 is illustrating an exemplary turbine unit support.

FIG. 6 is illustrating an exemplary turbine unit support 6000 wherein a turbine unit mounted on an inspiratory reservoir being a bellow. The turbine unit and the inspiratory reservoir includes a turbine housing 30, a turbine motor 31, a turbine motor base plate 32, a turbine gas inlet 33, a turbine gas outlet 34, a bellow support top plate 35, bellow support distances 36, a bellow 37, a bellow base plate 38, and a bellow top member 39 (such as a membrane). The arrow 40 illustrates an inlet flow 40 and the arrows 41 the distributed force.

The concept is that the vibrations from the turbine motor 31 are mechanically isolated from the turbine housing 30 where the unit is mounted. Additionally the heat generated in the turbine motor 31 is transferred to the inside of the bellow 37 via the turbine base plate 32 and bellow top member 39. This may cool the turbine unit which will increase its expected lifespan.

In this example, a gas inlet flow 40 is fed to the turbine gas inlet 33. The turbine motor 31 then compresses the gas and feed it to the turbine gas outlet 34, the arrow shows the direction of the flow. The gas flow continues into the inside of the bellow 37. The bellow 37 may then expand towards the bellow base plate 38. The bellow base plate 38 will then move opposite the distributed force 41. The distributed force 41 may consist of a package of springs or other means to generate a force.

When the turbine motor 31 is running, vibrations are generated. The vibrations may be isolated from the environment by the bellow top member 39 between the turbine motor base plate 32 and the bellow support top plate 35. In some examples, other soft parts may also to include in this area to improve vibration isolation.

Heat generated from the turbine motor 31 may be transferred to the gas inside the bellow 37 via the turbine motor base plate 32 and the bellow top member 39. Additionally, in some examples, a check valve (not shown) downstream the turbine gas outlet 34 may prohibit the pressurised gas inside the bellow 37 to leak back upstream the turbine when the turbine motor 31 is running at low speed or is stopped.

While several examples have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used.

The invention claimed is:

1. A turbine ventilator comprising:
    a first valve connectable to at least one breathing orifice of a subject;
    an inspiratory reservoir having an adjustable volume, said inspiratory reservoir is fluidically connectable to said first valve a turbine unit is fluidically connectable to the inspiratory reservoir, and said turbine unit is fluidically connectable via said first valve to the at least one breathing orifice of the subject; at least one first sensor to measure a flow or pressure; a sensor for measuring a fill ratio of the inspiratory reservoir; and
    a control unit is configured to control said first valve for controlling a flow or pressure from the inspiratory reservoir and/or turbine unit to the subject based on setpoints for said flow or pressure measured by the at least one first sensor, and for determining the fill ratio of the inspiratory reservoir based on a volume signal from the sensor;
    whereby the control unit controls the first valve during different stages of an inspiration phase, based on the setpoints; so that:
    an inhalation flow to the at least one breathing orifice of the subject is a combination of the flow from the inspiratory reservoir, and the turbine unit;
    the inhalation flow to the at least one breathing orifice of the subject is only from the turbine unit; and
    a flow from the turbine unit is used both for filling the inspiratory reservoir and as the inhalation flow.

2. The turbine ventilator of claim 1, further comprises a second valve arranged between the turbine unit and the inspiratory reservoir;
    wherein the control unit is configured to control said second valve to control a flow or pressure from the turbine unit to the inspiratory reservoir.

3. The turbine ventilator according to claim 2, wherein the control unit is configured to adjust said first valve and/or said second valve, thereby:
    fluidically connecting the turbine unit and the inspiratory reservoir to the at least one breathing orifice of the subject; or
    fluidically connecting the turbine unit to the at least one breathing orifice of the subject.

4. The turbine ventilator of claim 1, wherein the inspiratory reservoir is a bellow unit which is spring-loaded with a force constant independent of a filling ratio of a volume of the bellow unit.

5. The turbine ventilator of claim 1, wherein the turbine unit is a blower unit, or a fan unit.

6. The turbine ventilator of claim 1, wherein the at least one first sensor includes at least three pressure sensors, a first of said at least three pressure sensors is configured for measuring a pressure or flow from the turbine unit, a second of said at least three pressure sensors is configured for measuring a pressure or flow to the subject, and a third of said at least three pressure sensors is configured for measuring a pressure or flow from the inspiratory reservoir.

7. The turbine ventilator of claim 1, further comprising a support element which is arranged on one side of the inspiratory reservoir, the turbine unit is then mounted on the support element whereby vibrations from the turbine unit are isolated from the environment by the inspiratory reservoir.

8. The turbine ventilator of claim 1, further comprising a support element which is arranged on one side of the inspiratory reservoir, the turbine unit is then mounted on the support element whereby heat from the turbine unit is transferred to the inside of the inspiratory reservoir.

9. The turbine ventilator of claim 1, further comprising a flow sensor which transmits an inhalation flow signal to said control unit for controlling said flow or pressure.

10. The turbine ventilator of claim 6, wherein measured signals from said at least three pressure sensors are used in a feedback loop for controlling said flow or pressure from said turbine unit to said subject and/or said inspiratory reservoir.

11. A method for a fast response turbine ventilation comprising:
    measuring a flow or pressure of a fluid to a subject by at least one first sensor;
    measuring a volume signal using a second sensor for determining a fill ratio of the inspiratory reservoir;
    controlling a first valve for controlling a flow or pressure from an inspiratory reservoir and a turbine unit to the subject during different stages of an inspiration phase based on setpoints for said flow or pressure measured by said at least one first sensor so that:
    an inhalation flow to the at least one breathing orifice of the subject is a combination of the inspiratory reservoir, and the turbine unit;
    the inhalation flow to the at least one breathing orifice of the subject is only from the turbine unit; and
    a flow from the turbine unit is used both for filling the inspiratory reservoir and as the inhalation flow.

12. The method according to claim 11, comprising using measured signals from said at least one first sensor in a feedback loop for controlling said flow or pressure from said turbine unit to said subject and/or said inspiratory reservoir.

13. The turbine ventilator of claim 2, wherein the control unit is configured to adjust said first valve and/or said second valve, thereby:
    fluidically connecting the turbine unit to the inspiratory reservoir and to the at least one breathing orifice of the subject; and
    fluidically connecting the turbine unit to the inspiratory reservoir.

* * * * *